(12) United States Patent
Preuss et al.

(10) Patent No.: US 9,289,313 B2
(45) Date of Patent: Mar. 22, 2016

(54) INSERTION INSTRUMENT FOR INSERTING SOCKET INSETS INTO HIP SOCKETS FOR HIP ENDOPROSTHESES

(75) Inventors: Roman Preuss, Kirchheim Unter Teck (DE); Heike Wolf, Nürtingen (DE); Tobias Weiss, Ebersbach (DE); Thomas Kilchenmann, Horgen (CH); Götz Griesmayr, Winterbach (DE); Manuela Muhr-Schenk, Fellbach (DE)

(73) Assignee: CeramTec GmbH, Plochingen (DE)

( * ) Notice: Subject to any disclaimer, the term of this patent is extended or adjusted under 35 U.S.C. 154(b) by 72 days.

(21) Appl. No.: 13/703,195

(22) PCT Filed: Jun. 22, 2011

(86) PCT No.: PCT/EP2011/060455
§ 371 (c)(1),
(2), (4) Date: Dec. 18, 2012

(87) PCT Pub. No.: WO2011/161166
PCT Pub. Date: Dec. 29, 2011

(65) Prior Publication Data
US 2013/0158558 A1   Jun. 20, 2013

(30) Foreign Application Priority Data

Jun. 25, 2010  (DE) .......................... 10 2010 030 540
Feb. 24, 2011  (DE) .......................... 10 2011 004 689

(51) Int. Cl.
*A61F 2/46*   (2006.01)
*A61B 17/88*  (2006.01)
(Continued)

(52) U.S. Cl.
CPC ............... *A61F 2/4609* (2013.01); *A61B 17/88* (2013.01); *A61B 17/8872* (2013.01); *A61B 17/92* (2013.01); *A61F 2/46* (2013.01); *A61F 2/4603* (2013.01); *A61F 2/4637* (2013.01); *A61B 2017/922* (2013.01); *A61F 2/34* (2013.01); *A61F 2002/305* (2013.01); *A61F 2002/30378* (2013.01); *A61F 2002/30487* (2013.01)

(58) Field of Classification Search
CPC .... A61B 17/88; A61B 17/8872; A61B 17/92; A61B 2017/922; A61F 2/46; A61F 2/4603; A61F 2/4609; A61F 2/4637
USPC .................. 606/86 R, 91, 99, 100; 623/22.12
See application file for complete search history.

(56) References Cited

U.S. PATENT DOCUMENTS 6,468,281 B1   10/2002  Badorf et al.
8,425,576 B2 *  4/2013  Anderson et al. ............. 606/289
(Continued)

FOREIGN PATENT DOCUMENTS

DE   29 922 792 U1   3/2000
DE   10 148 022 A1   5/2003
(Continued)

*Primary Examiner* — Larry E Waggle, Jr.
(74) *Attorney, Agent, or Firm* — Norton Rose Fulbright US LLP

(57) ABSTRACT

An insertion instrument for instrumented insertion of a socket inset (4) with a spherical cap (20) into a hip socket (5) of a hip-joint prosthesis, having an impacting instrument (1) with a handle (7), at one end of which a holding tool for the socket inset (4) is located. In order to avoid tilting of the socket inset during insertion, it is proposed that the one end (8) of the impacting instrument (1) has a spherical shape and is part of the holding tool, and the holding tool furthermore comprises an impacting head (2), which is designed as a separate component and received the spherical end (8) of the impacting instrument (1) in an articulated manner, and an insertion aid (3), which is designed as a separate component and serves to hold the socket inset (4) on the outer geometry of the impacting head (2), and the impacting head (2) can be connected to the spherical end (8) to form a ball joint.

6 Claims, 20 Drawing Sheets

(51) Int. Cl.
*A61B 17/92* (2006.01)
*A61F 2/30* (2006.01)
*A61F 2/34* (2006.01)

(56) References Cited

U.S. PATENT DOCUMENTS

| | | | |
|---|---|---|---|
| 8,900,245 B2 * | 12/2014 | Splieth et al. | 606/99 |
| 2003/0060890 A1 * | 3/2003 | Tarabishy | 623/22.12 |
| 2010/0137870 A1 | 6/2010 | Shea et al. | |
| 2011/0245837 A1 | 10/2011 | Preuss et al. | |
| 2012/0303035 A1 | 11/2012 | Geebelen | |
| 2013/0331849 A1 * | 12/2013 | Splieth et al. | 606/99 |

FOREIGN PATENT DOCUMENTS

| | | |
|---|---|---|
| DE | 10 2009 054633 A1 | 6/2010 |
| FR | 2701206 A1 | 8/1994 |
| WO | 2008/106598 A1 | 9/2008 |
| WO | 2011/095575 A2 | 8/2011 |
| WO | WO 2011095575 A2 * | 8/2011 |

* cited by examiner

INSERTION INSTRUMENT FOR INSERTING SOCKET INSETS INTO HIP SOCKETS FOR HIP ENDOPROSTHESES

This application is a §371 of International Application No. PCDEP2011/060455 filed Jun. 22, 2011, and claims priority from German Patent Application Nos. 10 2010 030 540.5 filed Jun. 25, 2010 and 10 2011 004 689.5 filed Feb. 24, 2011.

FIELD OF THE INVENTION

The invention relates to an insertion instrument for instrumented insertion of a socket insert having a spherical cap into a hip socket of a hip joint prosthesis, said insertion instrument comprising an impacting instrument with a handle at one end of which a holding tool for the socket insert is located.

BACKGROUND OF THE INVENTION

There exists on the market a multiplicity of prosthesis systems for replacing the natural hip joint in the event of painful, traumatic, arthritic or other changes. Usually, so-called modular systems are used wherein a socket insert is inserted in a hip socket consisting in most cases of a metal alloy, which socket insert forms a part of the artificial sliding bearing and which can consist of a metal alloy, a ceramic material, a plastic or a composite of the aforementioned materials. Coupling between the socket insert and the hip socket often takes place through a so-called conical clamping, wherein a conically shaped portion of the outer geometry of the socket insert together with a matching conically shaped portion of the inner geometry of the hip socket forms a frictional connection, see FIG. 1.

One of the problems which may occur intra-operatively is the tilted insertion of the socket insert into the hip socket. Then, instead of the described conical clamping, jamming of the socket insert can occur between three contact points within the clamping cone of the hip socket. Depending on the magnitude of the force applied during clamping, such high frictional forces occur as a result of the punctual jamming that the position of the socket insert can no longer be corrected intra-operatively, see FIG. 2.

The consequences for the function of the hip joint prosthesis in the case of a socket insert that is inserted in a tilted manner substantially depend on the material of the socket insert and range from increased wear to corrosion and to complete destruction of the socket insert. Thus, a socket insert inserted in a tilted manner can be the cause for a subsequent, complicated and expensive revision surgery.

In order to avoid the tilted insertion of socket insert, a number of insertion instruments are available on the market. Their function is substantially based on the following three steps:

1. Gripping the socket insert at the upper outer edge.
2. Aligning the instrument including the socket insert relative to the hip socket so that the axes of symmetry of the hip socket and the socket insert run in parallel,
3. Abruptly and rapidly pushing the socket insert into the hip socket while releasing the grip and establishing the clamping connection.

EP 1 076 537 B1 and DE-U-299 22 792 describe insertion instruments wherein the socket insert is gripped at the upper edge by three holding claws. Furthermore, these insertion instruments provide a short handle piece at which the surgeon can grab the insertion instrument and can insert it together with the socket insert into the operating field. There, placing it onto the hip socket and finally joining the socket insert takes place. The disadvantages of these solutions—little feedback through palpation for the surgeon, required space for the instrument makes inserting and packaging difficult—are resolved by an insertion instrument according to DE 10 2009 054633.

Direct manual handling during which the hand is moved directly into the operating field and possibly touches the wound tissue is viewed by different surgeons as being disadvantageous. From the surgeons' view, this can result in an increased risk of infection. Furthermore, the visibility of the operating field is temporarily extremely limited. For the mentioned reasons, some surgeons prefer to carry out the handling of prosthesis components through instruments by means of a long handle and a handhold at the end.

WO 2008/106598 describes an insertion instrument wherein a kind of an elastic cover is pressed onto the socket insert. The edge of the cover engages with the socket insert over the entire circumference. Through an opening in the cover including a radial slot, an impacting instrument or the combination of socket insert and cover is attached onto an impacting instrument. By means of the impacting instrument, the socket insert is introduced into the operating field and joined.

The disadvantages of the described solution are:

Due to the radial slot in the cover opening, the coupling between cover and impacting instrument is slightly flexible; however, it does not permit any major tilting of the socket insert with the cover relative to the axis of the impacting instrument. This means, when introducing the socket insert into the operating field, the socket insert is aligned substantially perpendicular to the axis of the instrument handle. Thus, aligning the socket insert and the hip socket does not take place automatically, but has to be actively performed through the surgeon.

The edge of the cover encloses the entire circumference of the socket insert, and for a correct alignment of the socket insert relative to the hip socket, has also to rest over the entire circumference on the socket end face. If this is not possible due to protruding tissue rests, e.g., osteophytes, no correct alignment of the socket insert prior to impacting is possible. As a result, the risk of tilted insertion increases, or the instrument cannot be used.

Due to the complete enclosure of the socket insert by the cover, the view on the end face of the of the hip socket when inserting the socket insert is obstructed so that the correct alignment of the socket insert relative to the hip socket cannot be controlled visually.

OBJECT OF THE INVENTION

It is an object of the invention to improve an insertion instrument according to the present invention in such a manner that tilting during the insertion of the socket insert is precluded, and the insertion instrument comprises a handle-shaped impacting instrument.

DETAILED DESCRIPTION

Due to the fact that the one end of the handle-shaped impacting instrument is formed spherically and is part of the holding tool, and the holding tool, furthermore, comprises an impacting head which is designed as a separate component and serves for receiving the spherical end of the impacting instrument in an articulated manner, and further comprises an insertion aid which is designed as a separate component and serves for holding the socket insert on the outer geometry of the impacting head, and the impacting head can be connected to the spherical end thereby forming a ball joint, tilting of the socket insert during the insertion is precluded. The insertion instrument comprises a handle-shaped impacting instrument.

Preferably, the outer geometry of the impacting head is adapted to the geometry of the spherical cap of the socket insert so that the momentum during insertion is uniformly transmitted to the spherical cap in the socket insert.

In one embodiment, the impacting head has a spherical cap with a resilient cap edge into which the spherical end of the impacting instrument snaps during assembly, as a result of which detachably fastening the impacting head is simplified.

In a preferred embodiment, the insertion aid consists of a spring ring having radially projecting holding claws, wherein due to the resilience of the spring ring, the holding claws are radially displaceable, and at the outer end of the holding claws, axially projecting hooks (9) are arranged which, in the assembled state, rest with their holding face against the outer surface of the socket insert and, at the same time, the holding claws rest with their support surface on the edge of the socket insert. This makes it possible to avoid tilting.

Preferably, the edge of the spherical cap is coaxially surrounded by a circumferential groove. This groove can receive the spring ring of the insertion aid in the assembled state.

In a preferred embodiment, the spring ring and the holding claws are located in the assembled state in a plane above the spherical cap of the socket insert so that handling is simplified.

Preferably, a projection for limiting the movement of the ball joint is arranged above the spherical end of the impacting instrument. This projection is circumferentially formed on the handle.

In order that the insertion aid does not slip off the impacting instrument, preferably, the radial diameter of the impacting head is larger than the diameter of the spring ring of the insertion aid.

An insertion instrument according to the invention for instrumented insertion of a socket insert having a spherical cap into a hip socket of a hip joint prosthesis consists of
- an impacting instrument with a handle, the one end of which is spherically formed,
- an impacting head for receiving the spherical end of the impacting instrument in an articulated manner, and
- an insertion aid which is designed as a separate component and serves for detachably fastening the socket insert.

A method according to the invention for inserting a socket insert having a spherical cap into a hip socket of a hip joint prosthesis using an above-described insertion instrument is characterized in
  that first an impacting head that fits for the diameter of tribological pairing of the socket insert is put into the spherical cap of the socket insert,
  that subsequently an insertion aid that fits for the outer diameter of the socket insert is put over the socket insert in which the impacting head is inserted, and the holding claws of the insertion aid are pulled over the edge of the socket insert so that the socket insert is securely held by the holding claws,
  that subsequently the impacting head mounted in the socket insert is attached onto the spherical end of the impacting instrument and the snap connection ball-spherical cap is joined.

The further course of action during inserting is preferably characterized in
  that subsequently by means of the impacting instrument with the socket insert fastened thereto, the socket insert is moved into the hip socket until the holding claws of the insertion aid touch at their lower side the end face of the hip socket and the socket insert is aligned axially parallel to the hip socket,
  that subsequently a momentum is exerted onto the other free end of the impacting instrument and as a result, the impacting head abruptly accelerates the socket insert toward the hip socket and therefore the socket insert is pushed out of the holding claws and into the hip socket in a still aligned position until anchoring of the two components occurs.

BRIEF DESCRIPTION OF THE FIGURES

The invention is explained below in more detail by means of figures. Identical reference numbers designate identical objects.

FIG. 4c shows the section A-A according to FIG. 4b.

FIG. 5a shows a top view from above of an impacting head 2, and FIG. 5b shows the section A-A according to FIG. 5a.

FIG. 11a shows the insertion aid 3, the impacting head 2 and the socket insert 4 as individual parts prior to joining.

FIG. 11b shows the impacting head 2 inserted into the socket insert 4.

FIG. 11c shows the insertion aid 3 which is attached over the socket insert 4 with inserted impacting head 2 and the holding claws of which are pulled over the edge of the socket insert 4

FIG. 11d shows the joined components, i.e., the insertion aid 3, the impacting head 2 and the socket insert 4 prior to joining with the impacting instrument 1.

FIG. 11e shows the assembled state of the snap connection between the impacting instrument 1 and the impacting head 2.

FIG. 11f shows the state of the completely assembled set during insertion into the operating field prior to contact with the hip socket 5.

FIG. 11g shows the inserted socket insert 4 with the insertion aid 3 which rests with its lower side against the front side of the hip socket 5.

FIG. 11h shows the socket insert 4 anchored in the hip socket 5, and the individual components namely impacting head 2, impacting instrument 1 and insertion aid 3 which are still connected after being detached from the socket insert.

Figure 5:
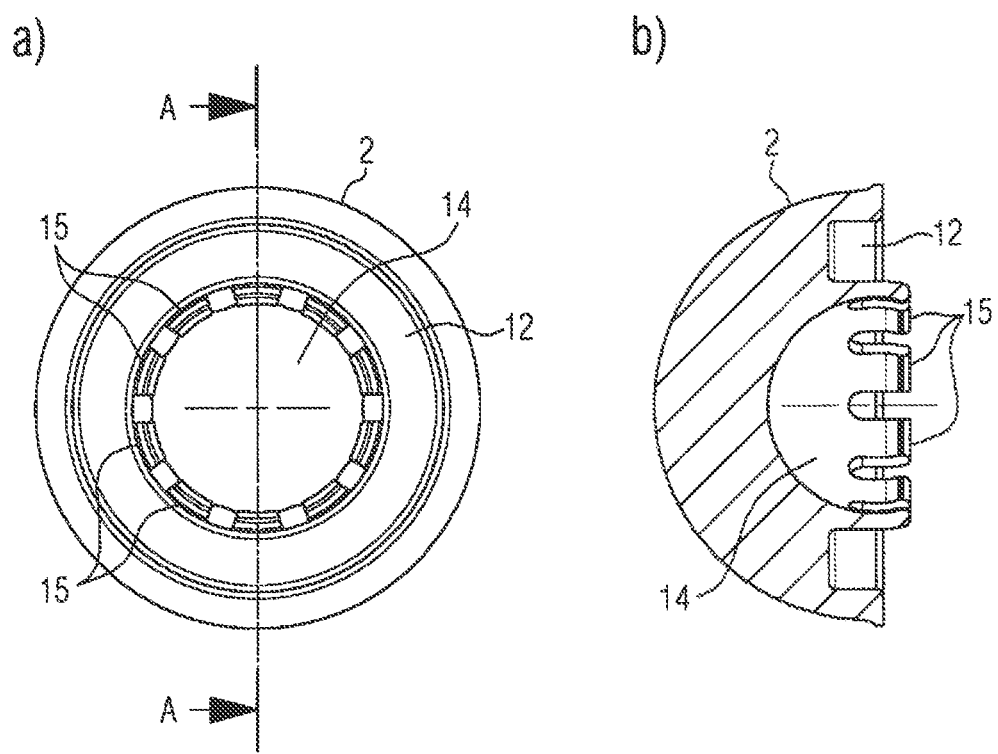
Figure 5C:
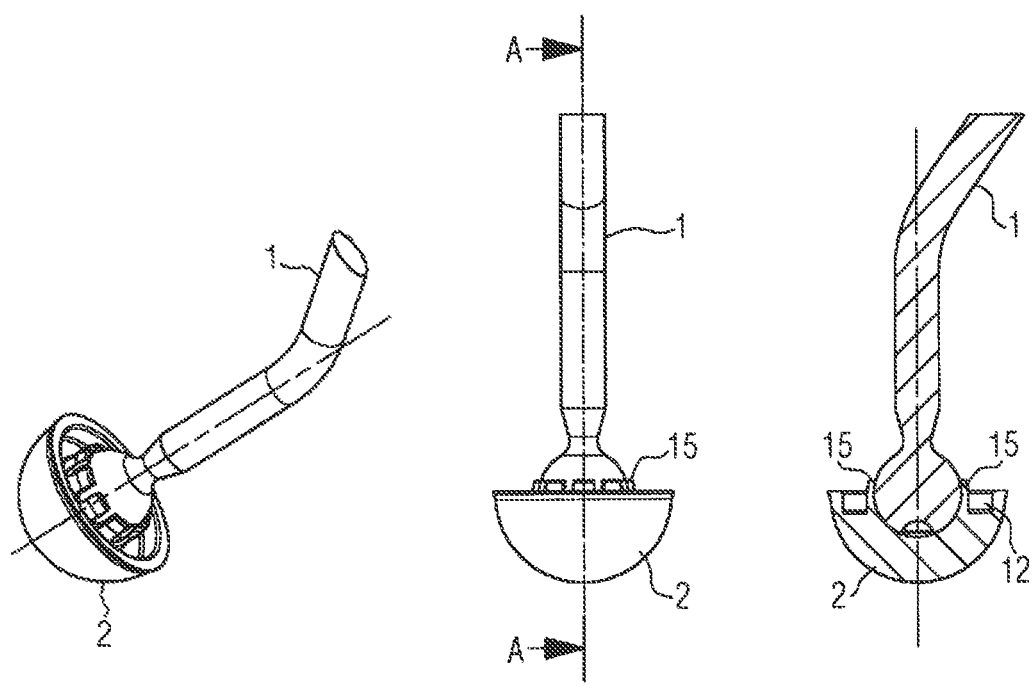
FIG. 5c shows the impacting instrument 1 with attached impacting head 2 in different views and in a section. The attachable impacting head 2 is provided with a circumferential groove 12 for receiving the spring ring 13 of the insertion aid 3. The spherical cap 14 has a resilient cap edge 15 that is raised beyond the ball equator. The impacting instrument 1 with the spherical end 8 is assembled with the impacting head 2 so as to form a ball joint.
Figure 6:
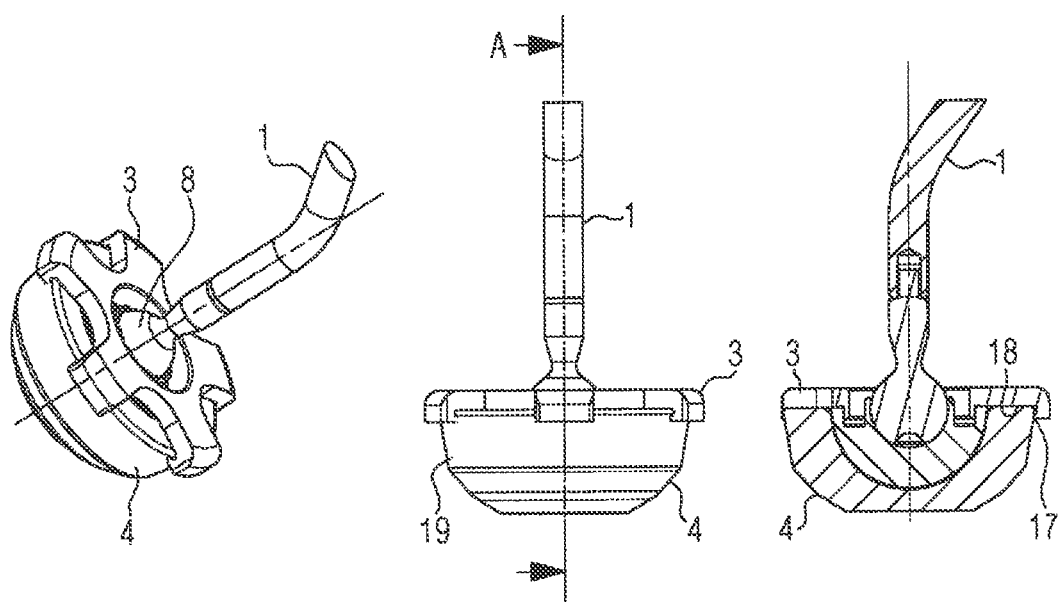
FIG. 6 shows the impacting instrument 1 assembled with the insertion aid 3, the impacting head 2 and the socket insert 4—ready for intra-operative insertion of the socket insert 4 into the hip socket 5.
Figure 7A:
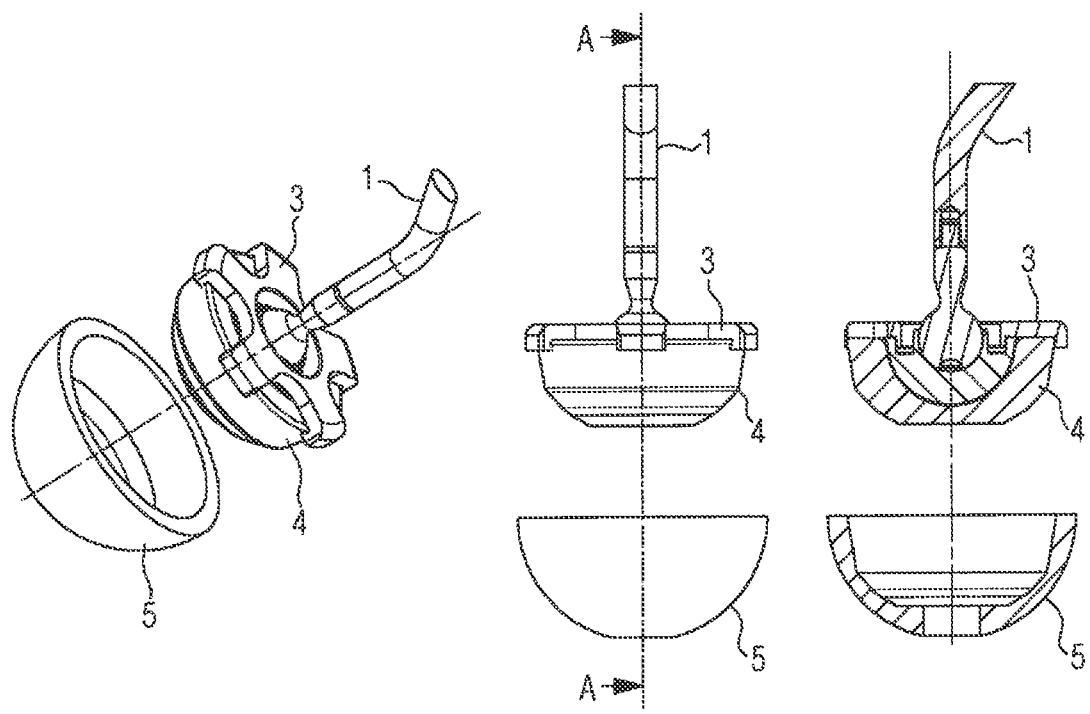
FIG. 7a shows the impacting instrument 1 assembled with the insertion aid 3, the impacting head 2 and the socket insert 4 prior to contact with the hip socket 5.
Figure 7B:
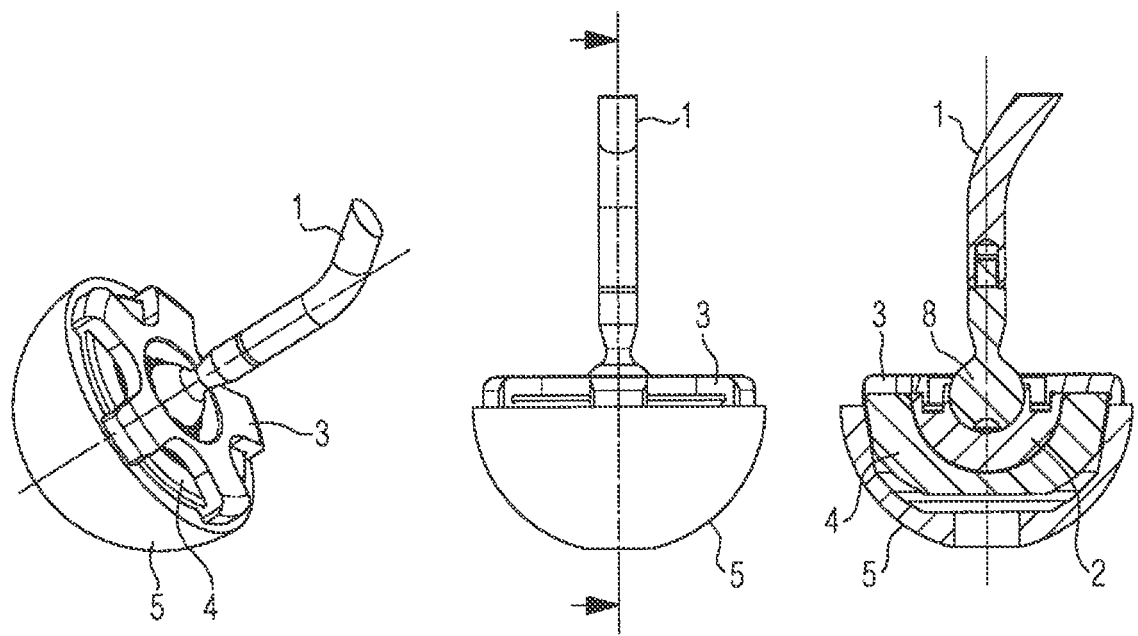
FIG. 7b shows it after attaching it onto the hip socket 5.

The inventive insertion instrument according to the Figures consists of an impacting instrument 1, an impacting head 2 and the insertion aid 3 and comprises the following functional elements or individual components:

An impacting instrument 1 with handhold 6, onto the end of which a hammer blow is exerted during impacting.
A handle 7 that is straight or cranked for minimally invasive techniques, the end of which faces away from the handhold 6 and ends as a ball 8.
Optionally, a projection 11 can also be provided near the spherical end or the ball 8, which projection acts as a mechanical stop for limiting the movement during the tilting of the coupled socket insert 4,
A spherical-segment-shaped impacting head 2 which approximately represents the ball head diameter that fits for the spherical cap of the socket insert 4. Furthermore, the impacting head 2 comprises a spherical cap 14 having a resilient cap edge 15 into which the spherical end or the ball 8 of the handle 7 snaps during assembly and thus forms a low-friction ball joint. Furthermore, the impacting head 2 comprises a circumferential groove 12 for receiving the resilient spring ring 13 of an insertion aid 3 according to DE 10 2009 054633—see e.g. FIG. 5.

The insertion instrument described here is intended as an expansion or additional instrumentation for an insertion instrument according to DE 2009 054633 (hereinafter designated as "insertion aid") and is preferably used in combination with the latter. It allows surgeons, which are critical of direct manual insertion of socket inserts, to handle and join the socket inserts by means of a "classical" instrument having a long handle 7 and a handhold 6 at the end thereof. The insertion aid according to DE 10 2009 054633 is preferably provided as a disposable product. The insertion instrument described herein, consisting of a small number of individual components, is preferably provided as repeatedly sterilizable instrumentation in the so-called screen.

The modular combination of insertion aid as a disposable product and the insertion instrument as a multi-use product offers a number of advantages compared to the integration of all functions in a reusable insertion instrument. The size range of the socket inserts depends on the diameter of the tribological pairing and on the outer diameter of the socket insert 4. In this connection it is market standard that there are socket inserts 4 having identical diameters of the tribological pairing but different outer diameters. The outer diameter usually depends on the diameter of the hip socket 5 into which the socket insert 4 is to be inserted. Furthermore, it is market standard to offer socket inserts 4 with different tribological pairing diameters for one outer diameter.

In order to be able to handle all these different socket inserts 4 with one reusable insertion instrument it would be necessary in the case of n tribological pairing diameters and m possible outer diameters to make exactly n×m impacting heads 2 available in the instrument set. In contrast to this, the modular solution of providing an additional insertion instrument for the existing insertion aid, as described herein, needs only n different impacting heads 2 for m different insertion aids 3.

Figure 11A:
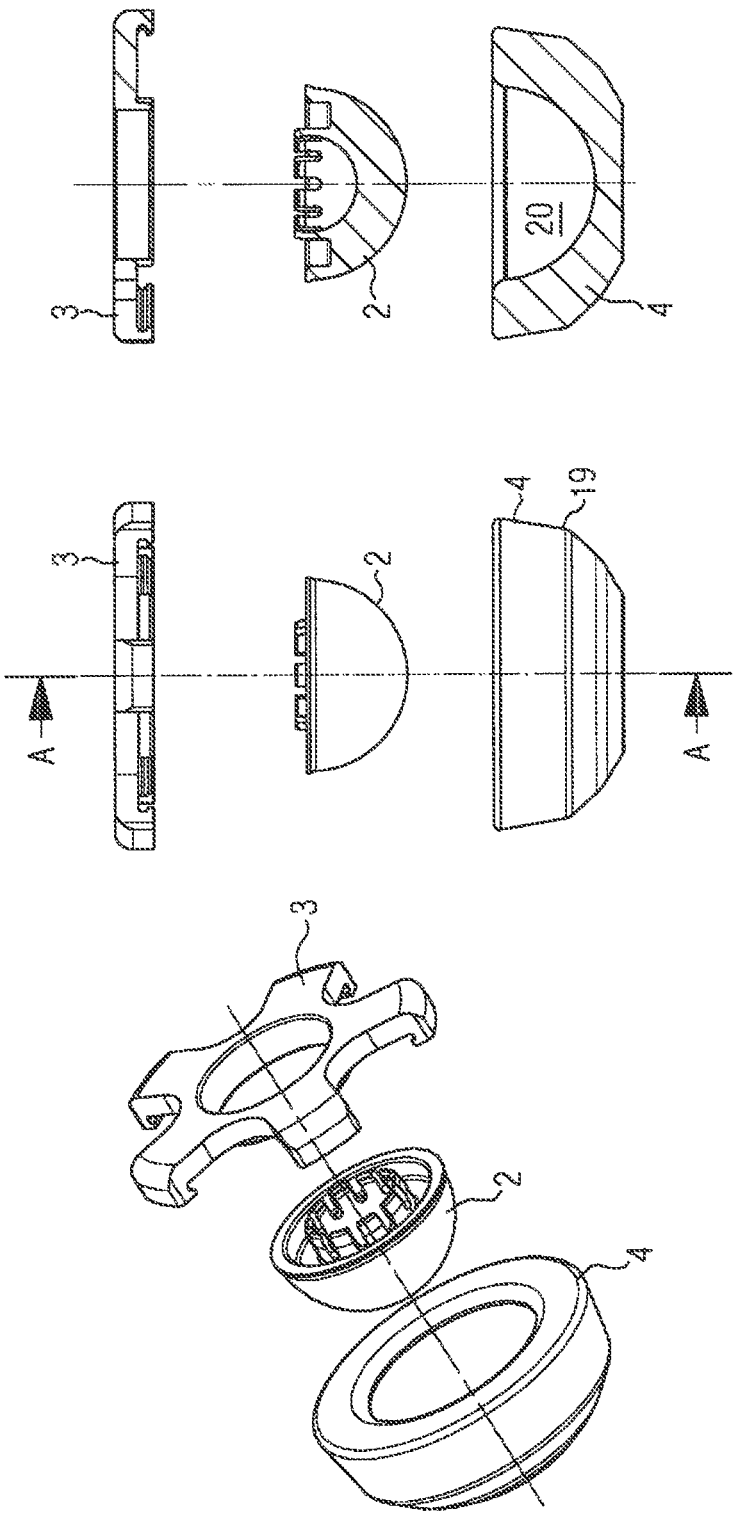
FIGS. 11a-h show the method according to the invention during the course of assembly.
Figure 11B:
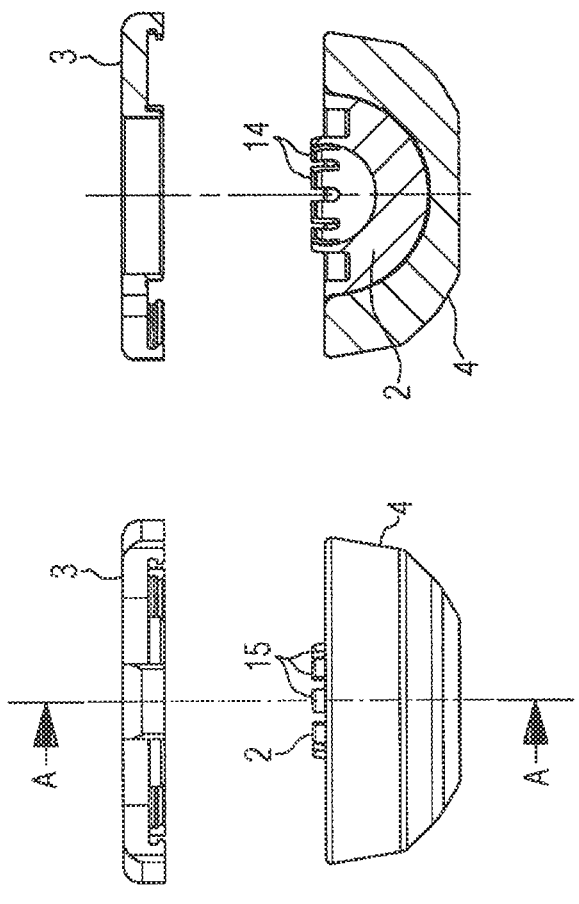
Figure 11B:
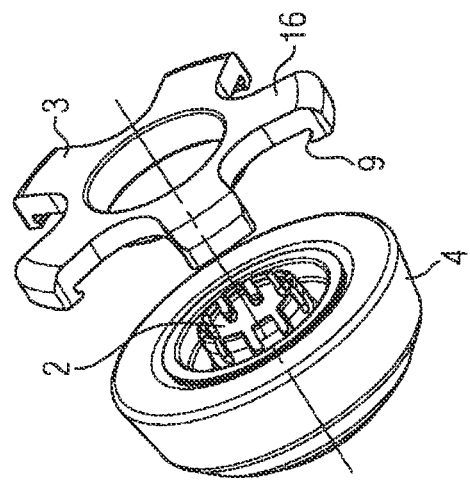
Figure 11C:
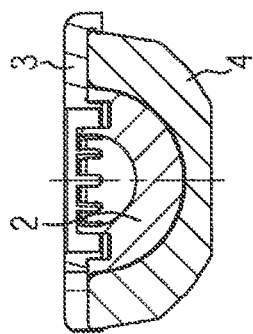
Figure 11C:
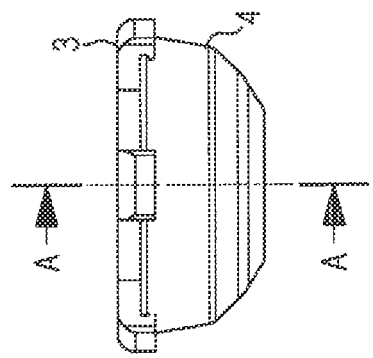
Figure 11C:
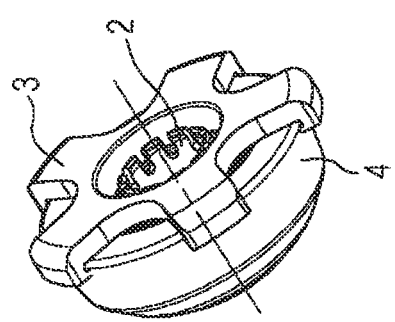
Figure 11D:
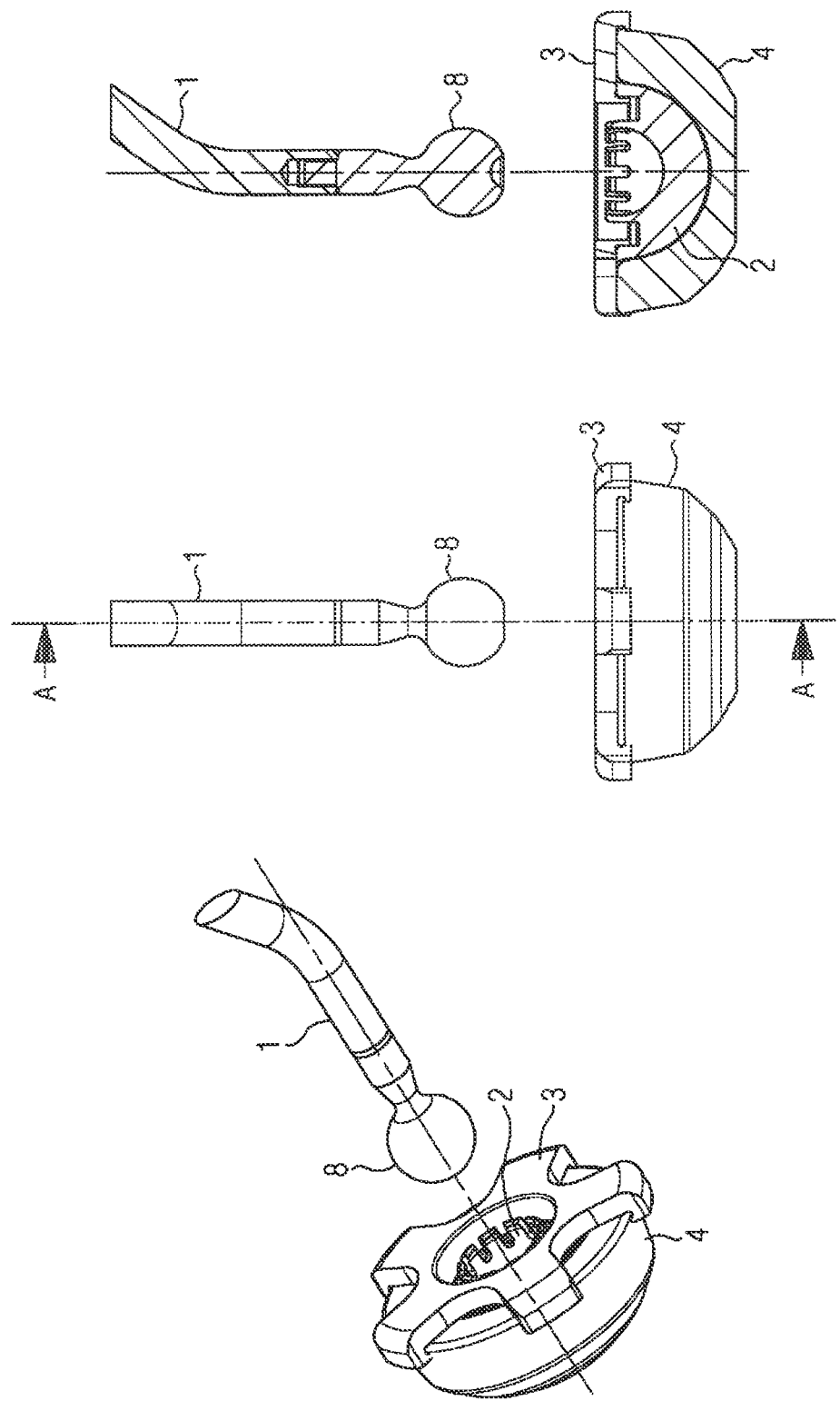
Figure 11E:
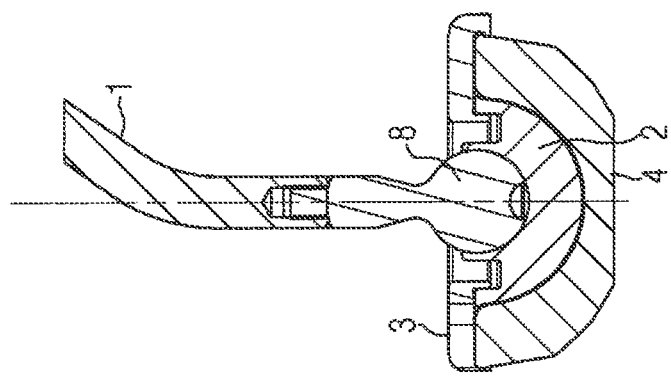
Figure 11E:
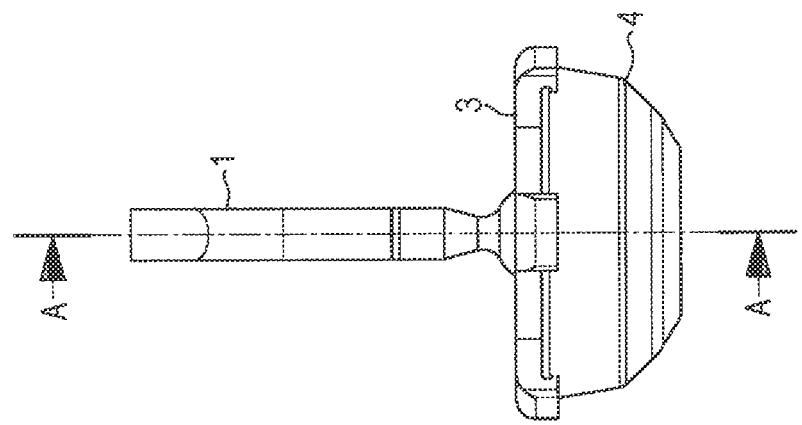
Figure 11E:
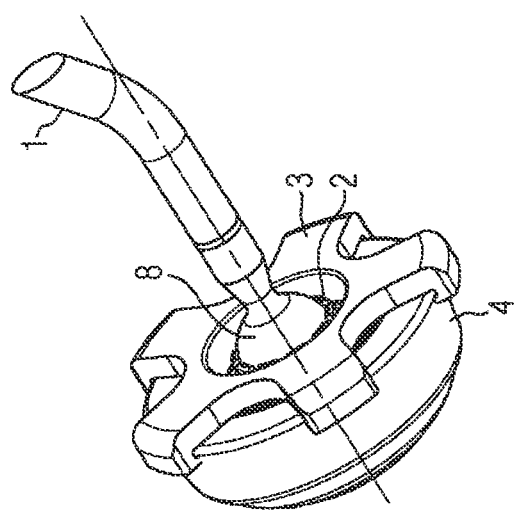

The intra-operative assembly of the components takes place such that first an impacting head 2 that fits for the diameter of tribological pairing of the socket insert 4 is put into the spherical cap of the socket insert 4. Subsequently, an insertion aid 3 that fits for the outer diameter of the socket insert 4 is put over the socket insert 4 in which the impacting head 2 is inserted, and the holding claws of the insertion aid 3 are pulled over the edge of the socket insert 4 so that the socket insert 4 is securely held by the holding claws—see FIGS. 11a to 11c. Then, the impacting head 2 mounted in the socket insert 4 is attached onto the spherical end of the impacting instrument 1 and the snap connection ball-spherical cap is joined. The socket insert 4 is now ready for handling and for instrumented intra-operative insertion, into the hip socket 5. In this connection, see FIGS. 11d-e.

The insertion begins with introducing the socket insert 4 into the operating field. The ball joint on the insertion instrument allows the socket insert 4 to tilt toward the axis of the handle 7 so that in the case of a minimal invasive access, "threading in" the socket insert 4 is made easier. Likewise, the ball joint allows the socket insert 4 or the holding claws 16 to laterally "bump" against the wound tissue or to "get caught" thereon without risking that the holding claws slip off the socket insert 4. In this case, the socket insert 4 tilts in the ball joint and slides unimpaired further into the operating field.

Figure 11F:
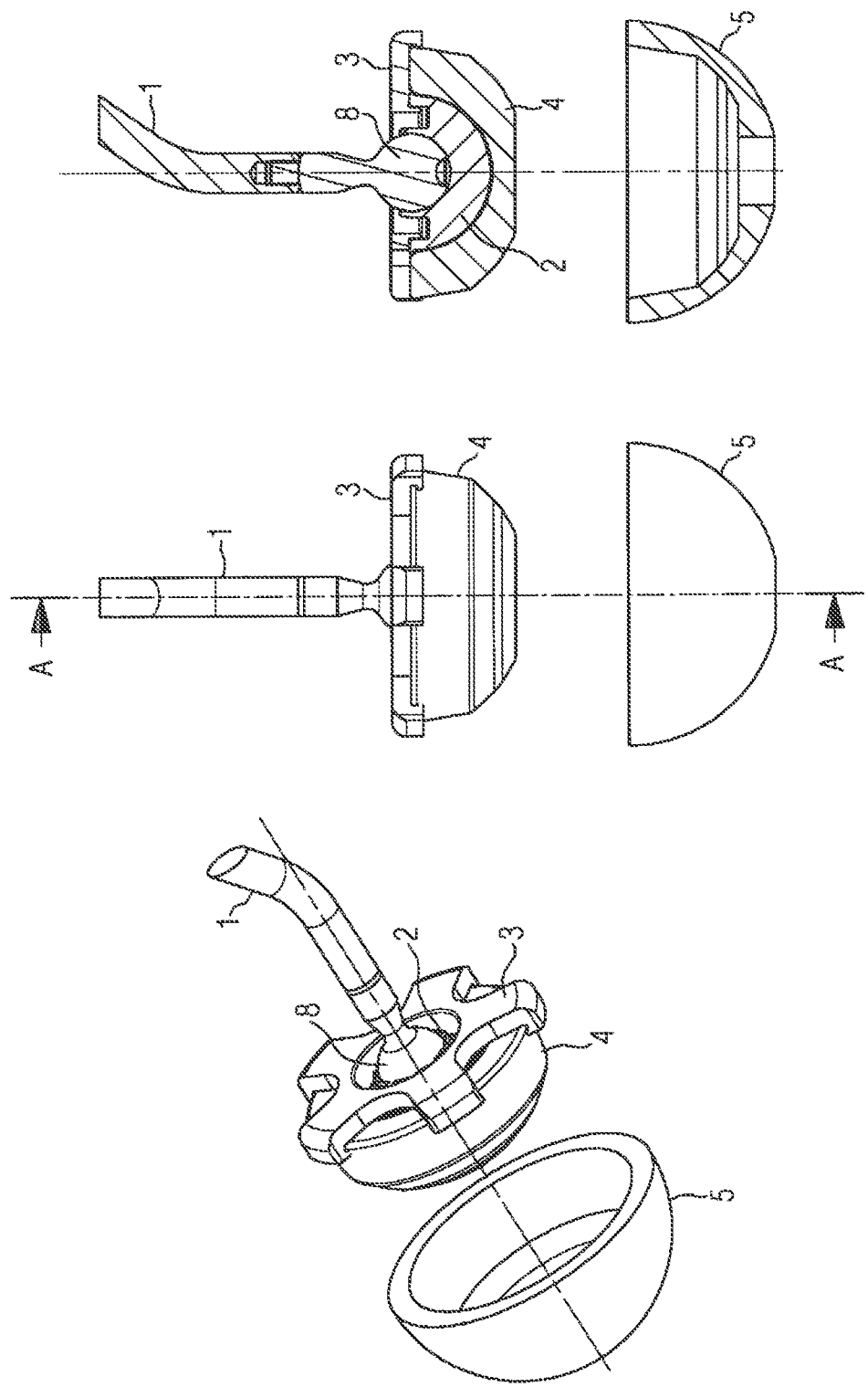
Figure 11G:
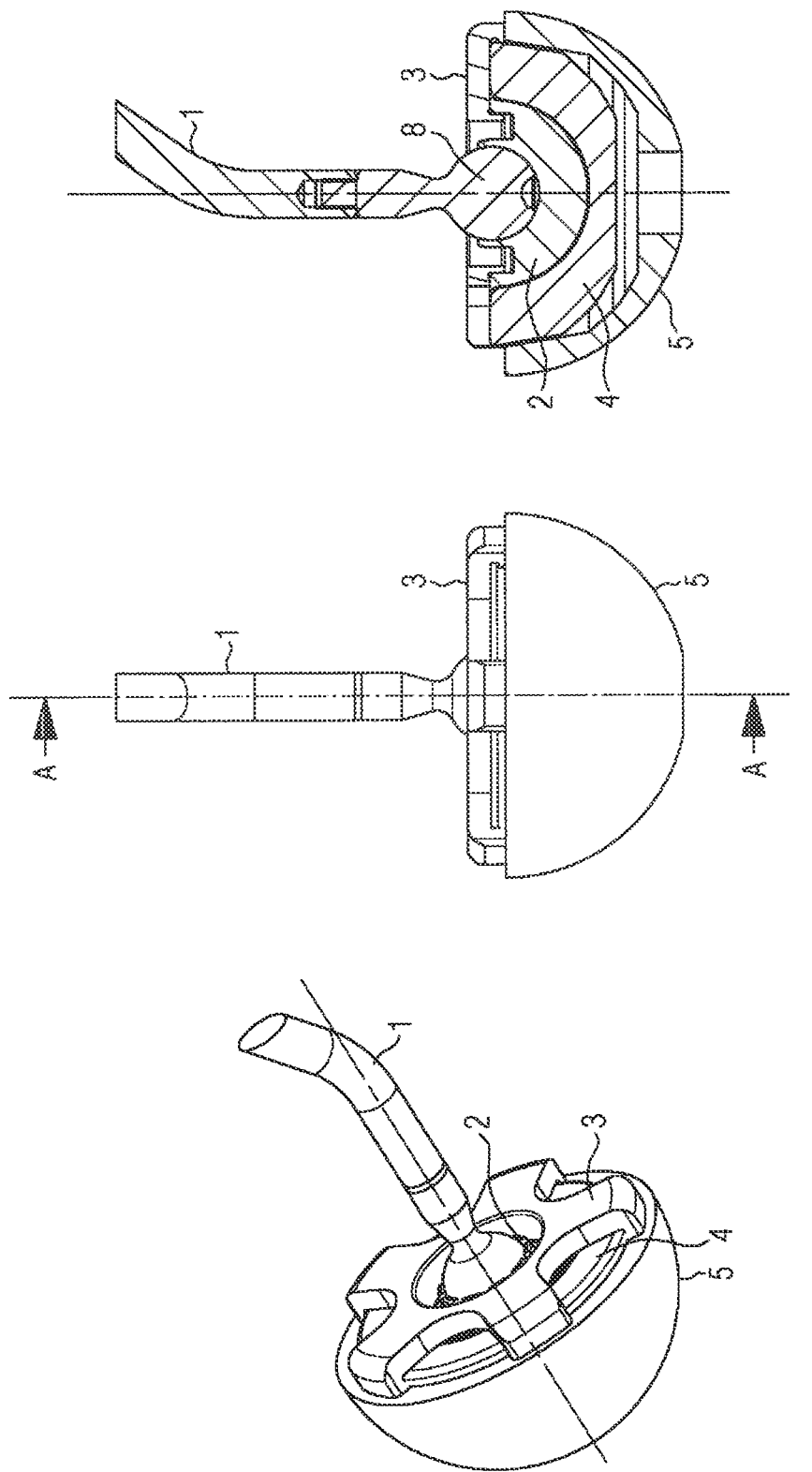

Finally, the socket insert 4 is moved into the hip socket 5 until the holding claws 16 touch with their lower side the end face of the hip socket 5. In this way, the socket insert 4 is aligned axially parallel to the hip socket 5. Due to the ball joint on the insertion instrument, this too is easier to achieve than it is with the previous solutions. In this connection, see FIGS. 11f-g.

Figure 11H:
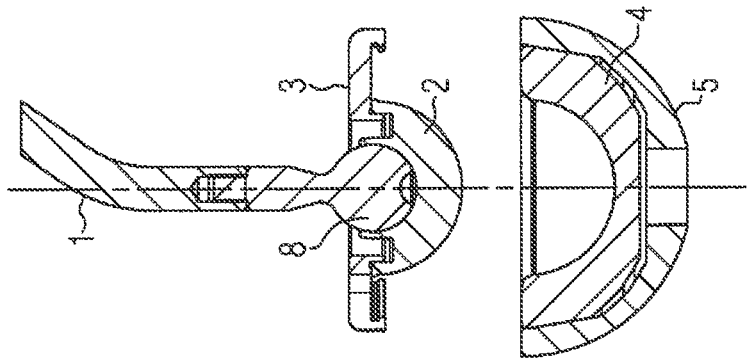
Figure 11H:
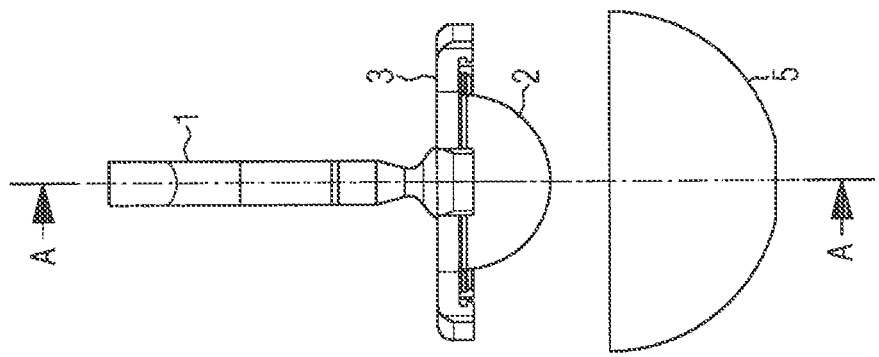
Figure 11H:
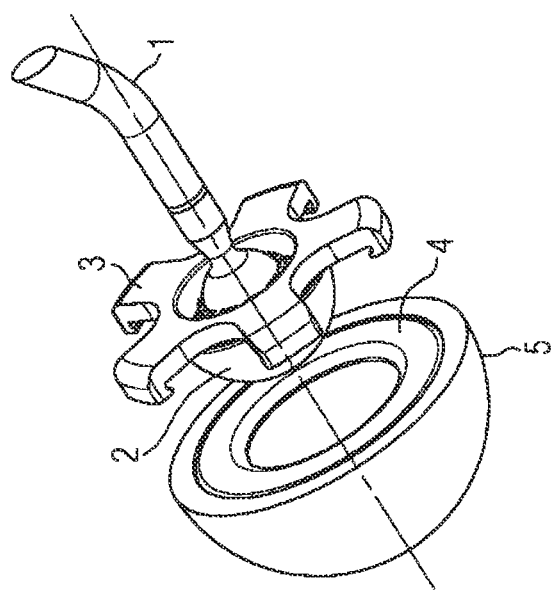

If the socket insert 4 and the hip socket 5 are aligned axially parallel, the socket insert 4 can be impacted—see FIG. 11h.

For this purpose, a momentum is exerted onto the free end of the handhold 6, e.g., by means of a conventional surgical hammer. The momentum is transferred through the handle 7 onto the impacting head 2. The impacting head abruptly moves the socket insert 4 toward the hip socket 5. As a result, the socket insert 4 is pushed out of the holding claws 16 and into the hip socket 5 in a still aligned position until anchoring of the two components occurs, e.g., by conical clamping 10. After disengaging the holding claws 16, the insertion aid 3 leaps a little upward on the handle 7 but remains securely attached to the handle 7

Depending on the recommendation of the prosthesis manufacturer, subsequently, further strokes for securely anchoring the components can be carried out. Subsequently, the insertion instrument is removed from the operating field. Due to the construction of the impacting head 2 it is ensured that the insertion aid 3 cannot accidentally remain in the operating field. Thus, the radial diameter of the impacting head 2 is larger than the diameter of the spring ring 13 of the insertion aid 3. As a result, the insertion aid 3 is removed by force from the operating field.

Described below are preferred inventive configurations of the insertion aid 3 as they can be used individually or in connection with the above-described impacting instrument 1 and the impacting head 2.

Figure 8:
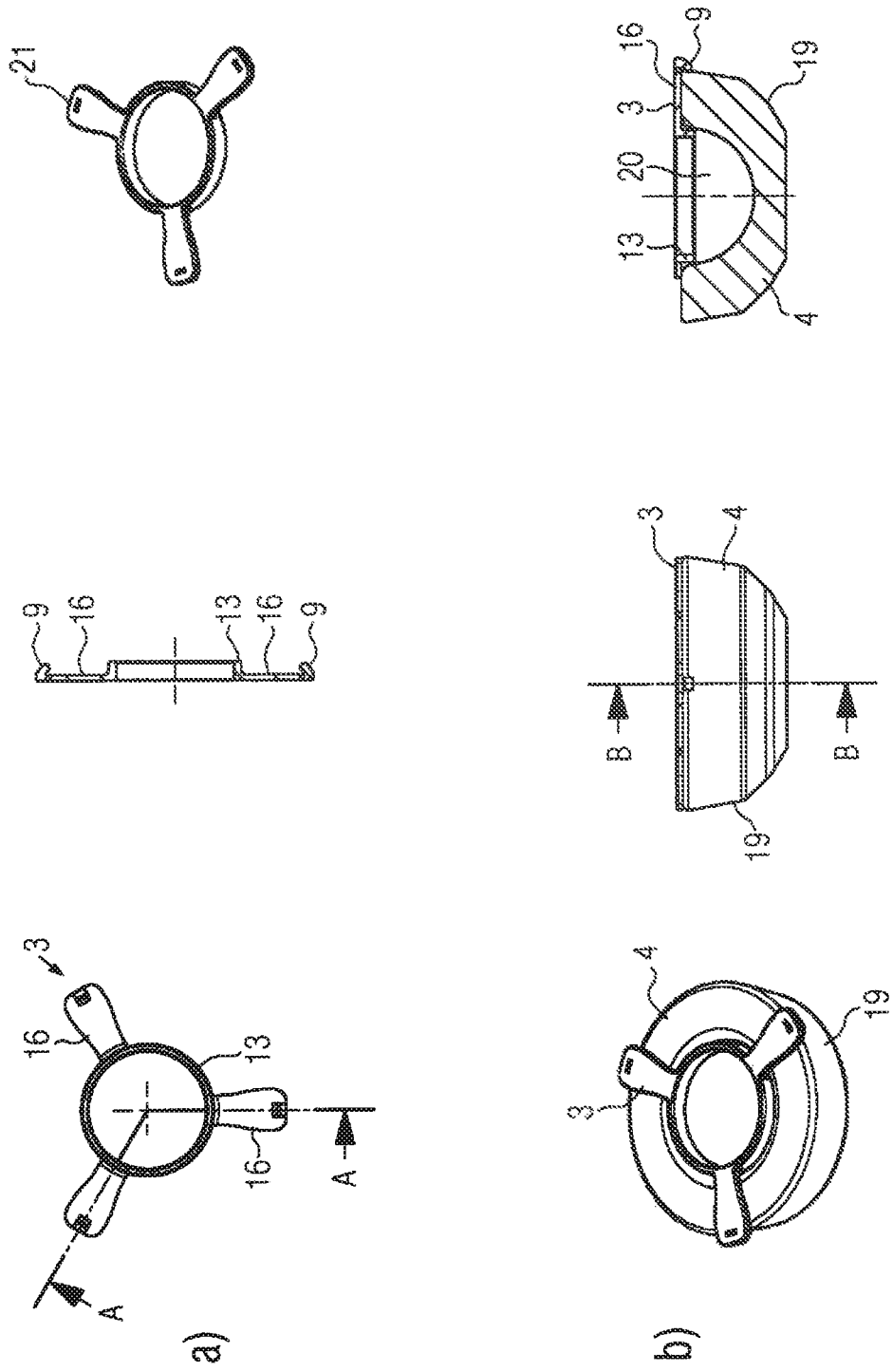
FIG. 8a shows an insertion aid 3 as a separate component that has 3 holding claws.
FIG. 8b shows it attached to and anchored on the socket insert 4.
FIG. 8c shows a section of FIG. 8b.
Figure 9:
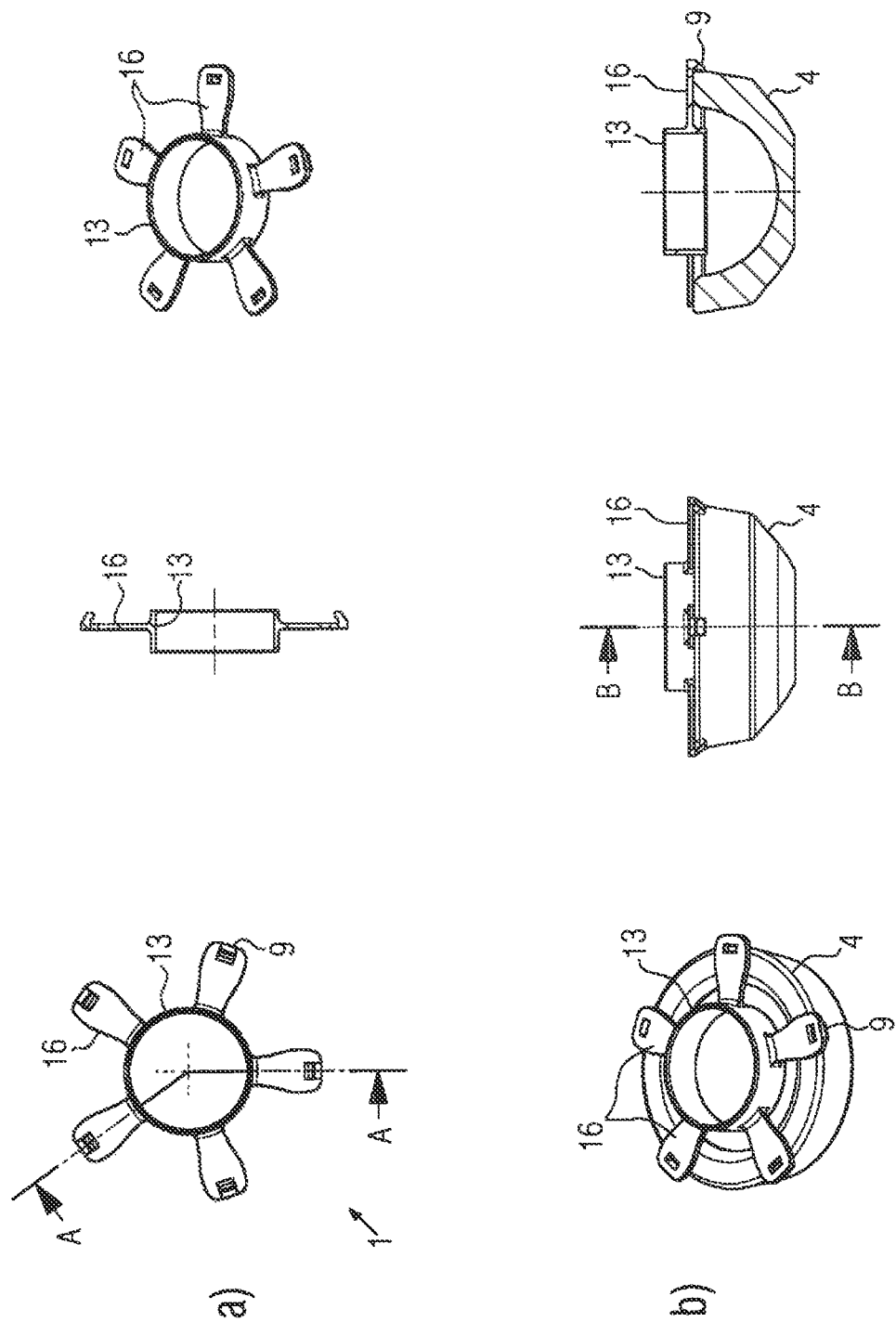
FIG. 9a shows an insertion aid 3 as a separate component that has 5 holding claws.
FIG. 9b shows it attached to and anchored on the socket insert 4.
FIG. 9c shows a section of FIG. 9b.
Figure 10:
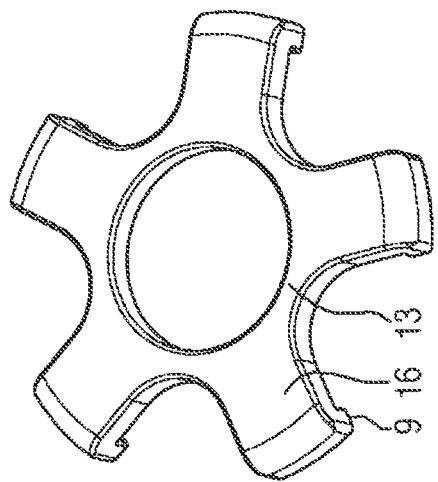
FIG. 10a shows an alternative insertion aid 3 as a separate component that also has 5 holding claws in a top view, FIG. 10a, FIG. 10b shows a section
FIG. 10c shows another view.
Figure 10:
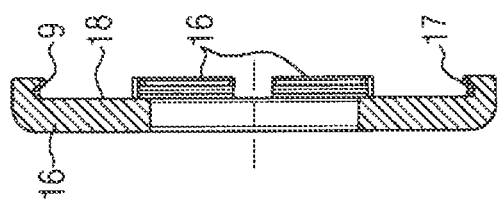
Figure 10:
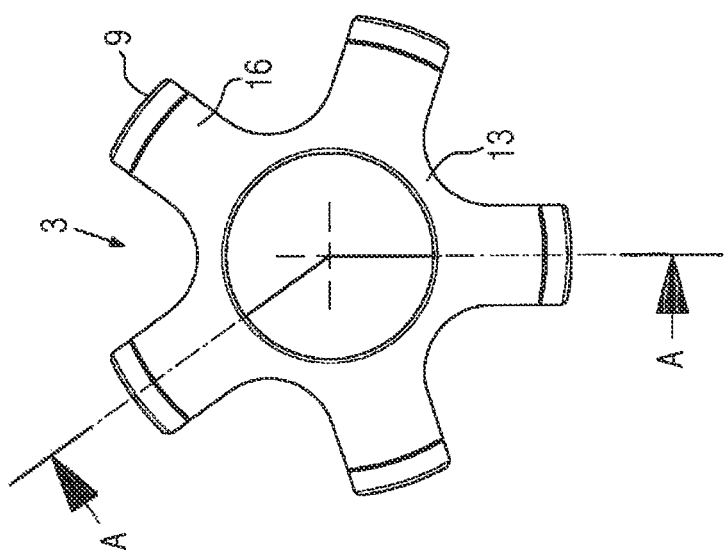

FIGS. 8, 9 and 10 show three insertion aids 3 according to the invention consisting of an annular resilient spring ring 13 with holding claws 16.

The insertion aid 3 (also referred to as insertion instrument) according to FIG. 8 consists in this embodiment of a resilient annular spring ring 13 to which three holding claws 16 are connected. In terms of manufacturing, the design of the insertion aid is advantageously implemented as a monolithic component which, e.g., can be produced by means of injection molding. The resilience of the insertion aid 3 results in that the holding claws 16 can be radially displaced. With progressing radial displacement of the holding claws 16, the spring force that needs to be overcome increases. The force-displacement curve of the holding claws 16 can be influenced through adequate geometrical configuration of the spring ring 13.

The holding claws 16 each have a holding surface 17 and a support surface 18 (see FIG. 10b). In the assembled state, the holding claws 16 rest with their support surface 18 on the end face of the socket insert 4. In the assembled state, the holding surfaces 17 rest against the outer surface 19 of the socket insert 4. Thus, in the assembled state, the holding claws 16 engage over the end face and the outer edge of the socket insert 4. Preferably, the spring ring 13 and the holding claws 16 are located in a plane above the spherical cap 20 of the socket insert 4. This makes it easier to grab the insertion aid 3.

FIG. 9 shows an alternative insertion aid 3 according to the invention with five holding claws 16 extending radially from the spring ring 13 at equal spacings.

According to the invention, the insertion aid 3 is dimensioned such that the holding claws 16 can be pushed over the outer edge of the socket insert 4 only by radially stretching said holding claws. This means, the spring ring 13 is deformed and a spring force acts on the holding claws 16. Thus, each holding surface 17 (see FIG. 9c) exerts a compressive force onto the socket insert 4, which compressive force is approximately equal to the spring force with regard to magnitude and direction. Through the compressive forces, frictional forces act also between the holding surfaces 17 and the outer surface 19 of the socket insert 4, which frictional forces counteract the withdrawal of the insertion aid 3 from the socket insert 4. This is essential for the function of the insertion aid 3.

FIG. 9b shows the socket insert 4 with the insertion aid 3 according to the invention in the assembled state.

When pushing the socket insert 4 with the assembled insertion aid 3 into a hip socket 5, the holding claws 16, at their lower end, come into contact with the end face of the hip socket 5. Since the holding claws all have the same downward expansion, the contact points form a plane which is parallel to the end face of the hip socket 5 and also to the end face of the socket insert 4. Thus, as a result, an alignment of the two end faces takes place at the same time so that they are parallel to each other. In this manner, a possible tilting of the socket insert 4 is counteracted. Due to the lateral gap still existing at this time between the socket insert 4 and the hip socket 5, a minor displacement of the socket insert 4 in the hip socket 5 is possible. By repeatedly pushing the socket insert 4 back and forth in the hip socket 5, the user has the possibility to check the correct position of the socket insert 4 in the hip socket 5. Specifically the easy displaceability and the bumping of the components provide the user with a very good palpatory feedback about the correct position of the socket insert 4 in the hip socket 5. This is the case if no impacting instrument 1 is used and the user replaces the impacting instrument 1 with his finger.

In order to finally push the socket insert 4 into the hip socket 5 until the frictionally engaging contact of the two cone surfaces on the outside of the socket insert 4 and the inside of the hip socket 5 occurs, the friction forces between the holding surfaces 17 of the insertion aid 3 and the outer surface 19 of the socket insert 4 have to be overcome. This takes place by a continuous or preferably by an abrupt increase of the axial joining force through the finger of the user. The socket insert 4 slides the remaining short distance into the hip socket 5, wherein significant tilting of the socket insert 4 is no longer possible. Possible minor tilting is compensated and corrected through the self-centering effect of the conical clamping connection.

At the outer ends of the holding claws 16, preferably, cuts 21 are arranged to facilitate the production using the injection molding method.

The embodiment of the insertion aid 3 having five instead of only three holding claws 16 has the advantage of a significantly stronger clamping of the socket insert 4. In addition, in the worst case, if a holding claw disengages or breaks during the application, the function of the insertion into the hip socket 5 is still ensured.

The spring ring 13 (see FIG. 9), which in the assembled state of the insertion aid 3 protrudes upward beyond the end face of the socket insert 4, gives the user a better handling/feel when grasping in the assembled state. The axial height h of the spring ring 13 (see FIG. 9) in the embodiment according to FIG. 9 preferably ranges between 6 and 12 mm, particularly preferred between 8 and 10 mm, and is approximately 9 mm in a special embodiment.

Apart from the standard disengagement by means of inserting a finger and axially pressing onto the spherical cap bottom of the socket insert 4 at the same time, the mentioned height h of the spring ring 13 allows an additional possibility of disengagement. By grasping the spring ring 13 and simply pressing the spring ring 13 from above, the holding connection likewise disengages and the socket insert 4 is pushed into the hip socket 5 and is positioned and anchored there by means of conical clamping.

Figure 1:
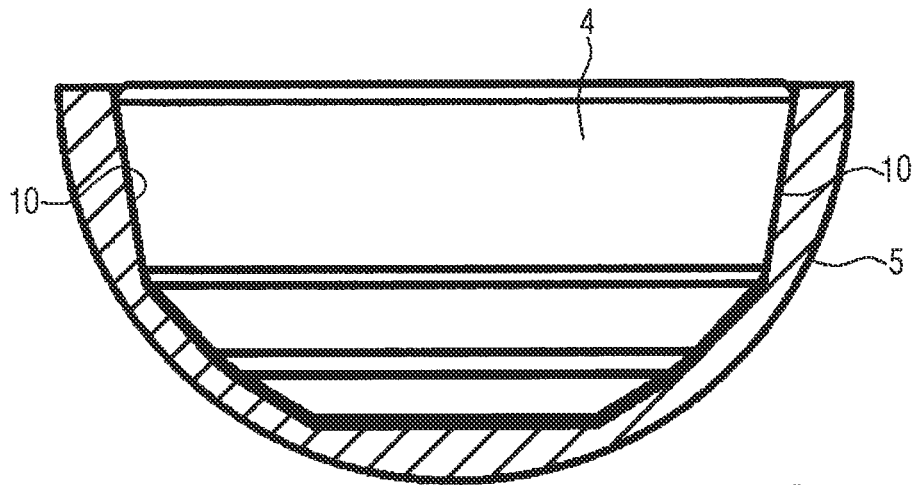
FIG. 1 shows a hip socket 5 into which a socket insert 4 is correctly inserted by means of conical clamping 10.
Figure 2:
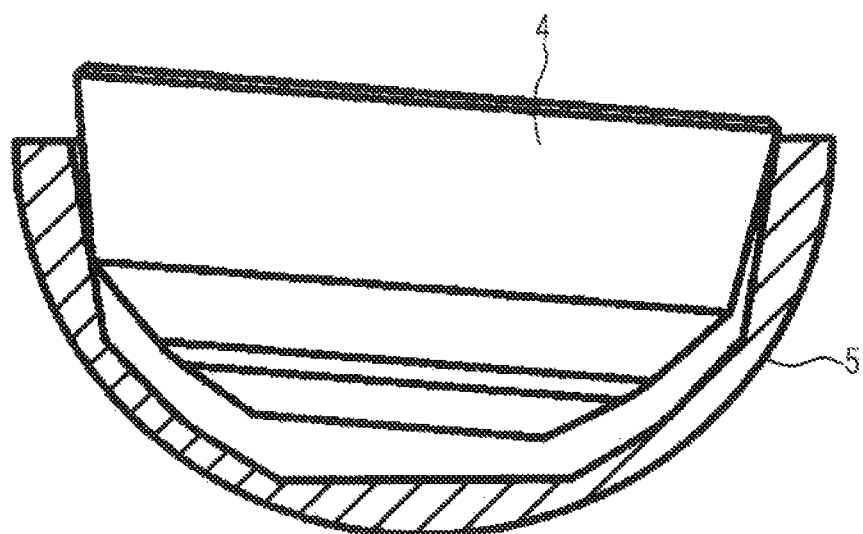
FIG. 2 shows a hip socket 5 into which a socket insert 4 is inserted tilted. The intended conical clamping 10 does not take effect. This is to be avoided.
Figure 3:
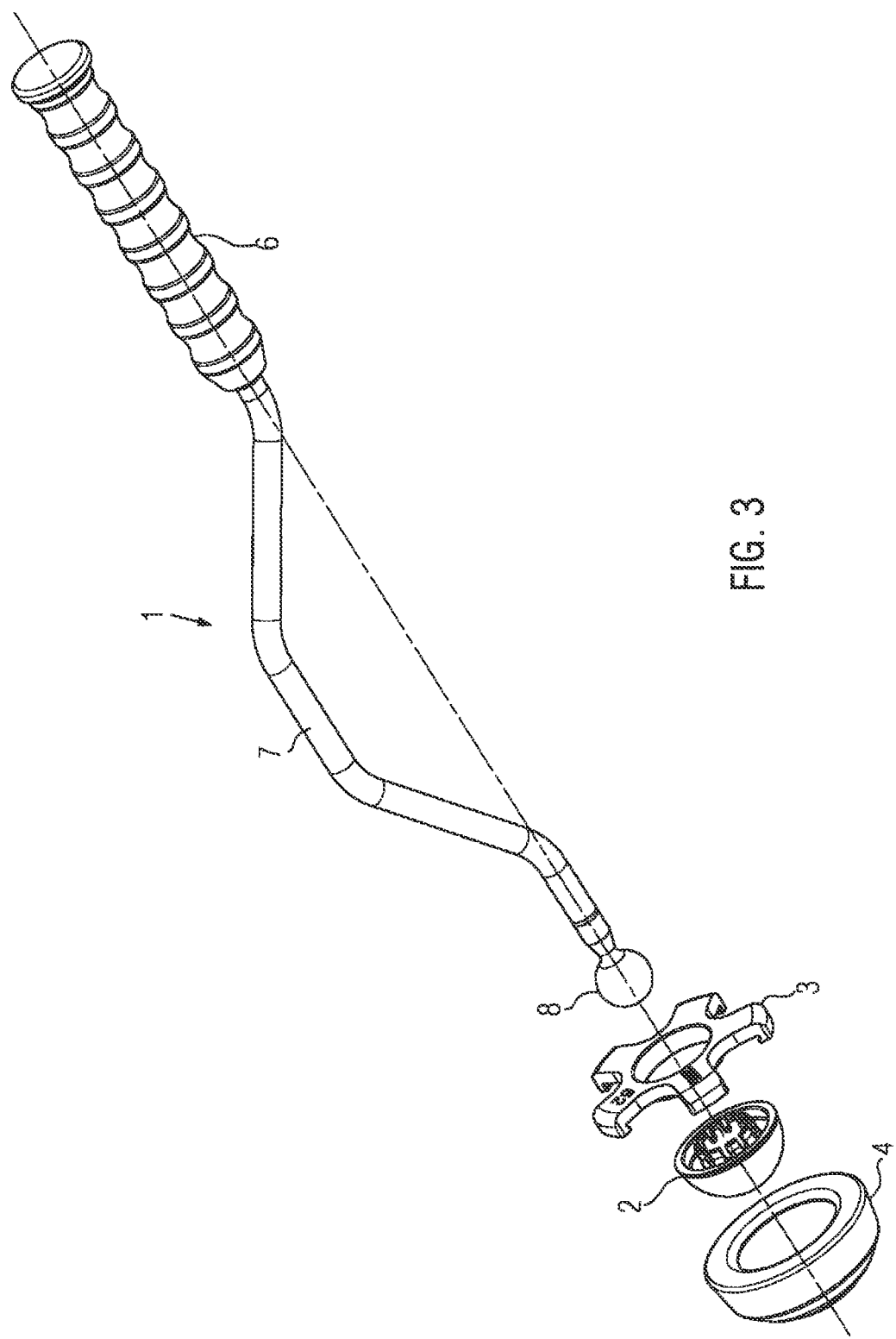
FIG. 3 shows the insertion instrument consisting of the impacting instrument 1 with a handhold 6, a handle 7, and a spherical end 8 which is a part of a ball joint, and an attachable impacting head 2 having a spherical cap as the second part of the ball joint for receiving the spherical end 8, and an insertion aid 3.
Figure 4A:
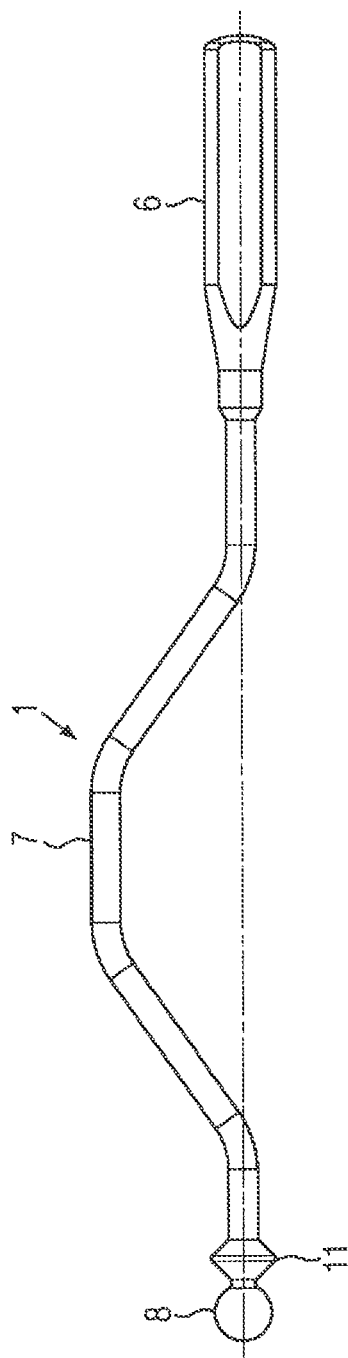
FIG. 4a shows an impacting instrument 1 with a handle 7 that transitions at one end into a handhold 6 and has on the opposite side a spherical end 8 as part of a ball joint. In the illustrated embodiment, the handle 7 is cranked. At the spherical end 8, a projection 11 is arranged as a tilting stop.
Figure 4B:
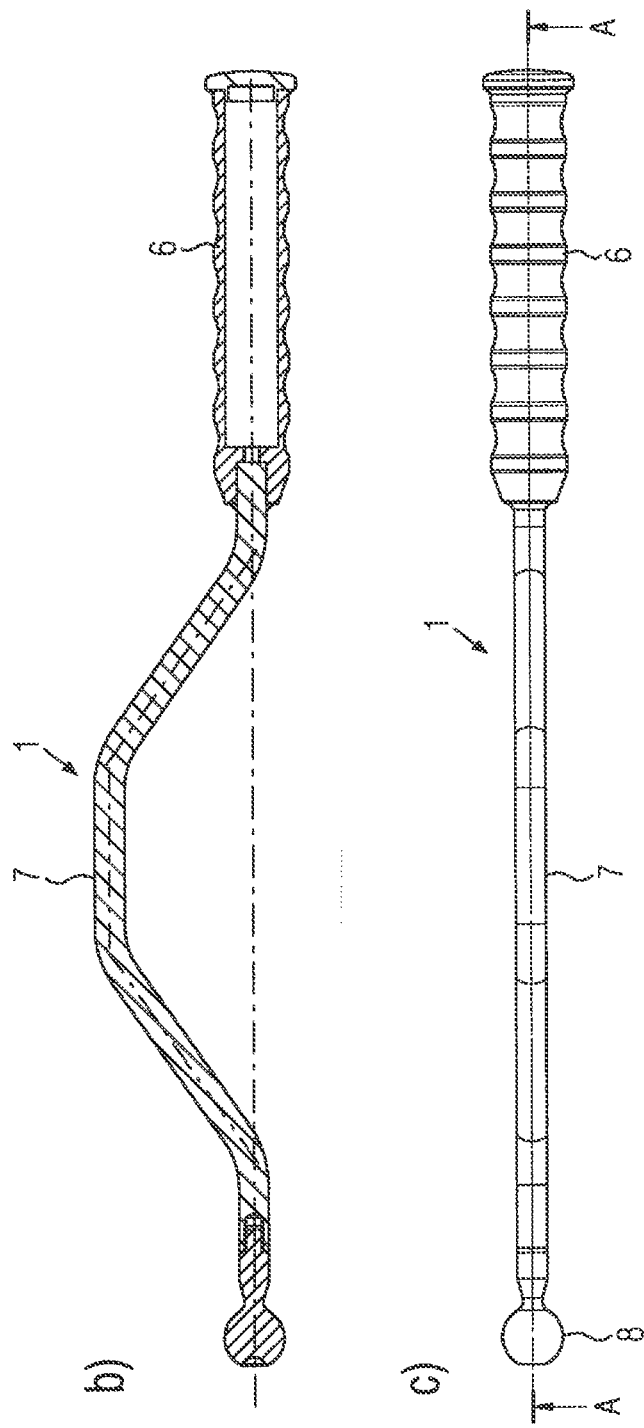
FIG. 4b shows an alternative impacting instrument 1 without tilting stop.

As described above, instead of the fingers, the impacting instrument 1 with impacting head 2 can be used. Both types of application (finger or impacting instrument 1) lead to the same result, namely a durable, stable anchoring of the socket insert 4 in the hip insert 5, as shown in FIG. 1. A socket insert 4 that is inserted in a tilted manner, as shown in FIG. 2, is precluded.

FIG. 10, as already mentioned, shows another insertion aid 3 according to the invention with five holding claws 16 which extend radially from the spring ring 13 at equal spacings.

In this embodiment, the insertion aid 3 is dimensioned such that the holding claws 16 can be pushed over the outer edge of the socket insert 4 only by radially stretching said holding claws. This means, the spring ring 13 is deformed and a spring force acts on the holding claws 16. Thus, each holding claw 16 exerts through its holding surface 17 (see FIG. 10c) a compressive force onto the socket insert 4, which compressive force is approximately equal to the spring force at the respective holding claw 16 with regard to magnitude and direction. This is essential for the function of the insertion aid 3.

The shape of the insertion aid is implemented here with increased use of material across the complete component.

The transition between the spring ring 13 and the holding claws 16 is designed in a flowingly curved manner. The spring ring 13 and the holding claws 16 preferably have the same axial height, which ranges between 3 and 5 mm.

The holding claws 16 with the holding surfaces 17 are all designed with identical width. Said width preferably ranges between 10 and 14 mm and is approximately 12 mm in a special embodiment. The direct holding surfaces 17 are preferably radially adapted to the outer surface 19 of the socket insert 4. Through the resulting larger contact surface, the friction forces are increased.

The geometrical configuration increases the stiffness of the component leading to the advantage of a significantly stronger clamping of the socket insert. The resistance against disengaging the insertion aid 3 from the socket insert 4 upon contact with the surroundings is therefore increased.

Due to the high clamping force or the disengagement force to be overcome, the insertion aid 3, the impacting instrument 1 and the impacting head 2 fit together extremely well.

In order to evenly position the socket insert 4 when overcoming the friction forces between the holding surfaces 17 of the insertion aid 3 and the outer surface 19 of the socket insert 4, an abrupt increase of the axial joining force through a light blow with the flat of the hand onto the end of the impacting instrument 1 is recommended.

The insertion aid 3 described herein is preferably provided as repeatedly sterilizable product together with the impacting instrument 1 and the impacting head 2 in the so-called screen. The selection of the material of the insertion aid meets the requirements with regard to resistance in the case of repeated treatment cycles (steam sterilization at 134° C.).

The invention claimed is:

1. An insertion instrument for instrumented insertion of a socket insert having a spherical cap into a hip socket of a hip joint prosthesis comprising:
    an impacting instrument with a handle;
    a holding tool for the socket insert located at the end of the handle;
    wherein the end of the impacting instrument is spherically formed and is part of the holding tool; and
    wherein the holding tool further comprises an impacting head which is designed as a separate component and serves for receiving the spherical end of the impacting instrument in an articulated manner; and
    an insertion aid which is designed as a separate component and serves for holding the socket insert on the outer geometry of the impacting head; and
    wherein the impacting head can be connected to the spherical end, thereby forming a ball joint, wherein the insertion aid comprises a spring ring having radially projecting holding claws, wherein due to the resilience of the spring ring, the holding claws are radially displaceable, and at an outer end of the holding claws, axially projecting hooks are arranged which, in an assembled state, rest with their holding surface against an outer surface of the socket insert and, at the same time, the holding claws rest with their support surface on an edge of the socket insert.

2. The insertion instrument according to claim 1, wherein in the assembled state, the spring ring and the holding claws lie in a plane above the spherical cap of the socket insert.

3. The insertion instrument according to claim 1, wherein a radial diameter of the impacting head is larger than the diameter of the spring ring of the insertion aid.

4. A method for inserting a socket insert having a spherical cap into a hip socket of a hip joint prosthesis using an insertion instrument, wherein the insertion instrument is for instrumented insertion of a socket insert having a spherical cap into a hip socket of a hip joint prosthesis comprising:
    an impacting instrument with a handle;
    a holding tool for the socket insert located at the end of the handle;
    wherein the end of the impacting instrument is spherically formed and is part of the holding tool; and
    wherein the holding tool further comprises an impacting head which is designed as a separate component and serves for receiving the spherical end of the impacting instrument in an articulated manner; and
    an insertion aid which is designed as a separate component and serves for holding the socket insert on the outer geometry of the impacting head; and
    wherein the impacting head can be connected to the spherical end, thereby forming a ball joint, wherein the method comprises:
    first, putting the impacting head that fits for the diameter of tribological pairing of the socket insert into the spherical cap of the socket insert;
    subsequently, putting the insertion aid that fits for the outer diameter of the socket insert over the socket insert in which the impacting head is inserted, and holding claws of the insertion aid are pulled over an edge of the socket insert so that the socket insert is securely held by the holding claws; and
    subsequently, attaching the impacting head mounted in the socket insert onto the spherical end of the impacting instrument and the ball joint is formed.

5. The method according to claim 4, wherein subsequently moving, via the impacting instrument with the socket insert fastened thereto, the socket insert into the hip socket until the holding claws of the insertion aid touch at their lower side the end face of the hip socket and the socket insert is aligned axially parallel to the hip socket;
    subsequently exerting a momentum on the other free end of the impacting instrument and as a result, the impacting head abruptly accelerates the socket insert toward the hip socket and therefore the socket insert is pushed out of the holding claws and into the hip socket in a still aligned position until anchoring of the two components occurs.

6. An insertion instrument for instrumented insertion of a socket insert having a spherical cap into a hip socket of a hip joint prosthesis comprising:
    an impacting instrument with a handle;
    a holding tool for the socket insert located at the end of the handle;
    wherein the end of the impacting instrument is spherically formed and is part of the holding tool; and
    wherein the holding tool further comprises an impacting head which is designed as a separate component and serves for receiving the spherical end of the impacting instrument in an articulated manner; and
    an insertion aid which is designed as a separate component and serves for holding the socket insert on the outer geometry of the impacting head; and
    wherein the impacting head can be connected to the spherical end, thereby forming a ball joint,
    wherein the outer geometry of the impacting head is adapted to the geometry of the spherical cap of the socket insert,
    wherein the insertion aid comprises a spring ring having radially projecting holding claws, wherein due to the resilience of the spring ring, the holding claws are radially displaceable, and at an outer end of the holding claws, axially projecting hooks are arranged which, in an assembled state, rest with their holding surface against an outer surface of the socket insert and, at the same time, the holding claws rest with their support surface on an edge of the socket insert.

* * * * *